United States Patent [19]

Steiniger et al.

[11] Patent Number: 5,000,832

[45] Date of Patent: Mar. 19, 1991

[54] PURIFICATION OF AQUEOUS GLYOXAL SOLUTIONS

[75] Inventors: Michael Steiniger, Neustadt; Hartwig Voss, Frankenthal; Leopold Hupfer, Friedelsheim, all of Fed. Rep. of Germany

[73] Assignee: BASF Aktiengesellschaft, Ludwigshafen, Fed. Rep. of Germany

[21] Appl. No.: 448,215

[22] Filed: Dec. 11, 1989

[30] Foreign Application Priority Data

Jan. 9, 1989 [DE] Fed. Rep. of Germany ....... 3900379

[51] Int. Cl.$^5$ ............................................. B01D 13/02
[52] U.S. Cl. ................... 204/182.4; 204/131; 204/182.3; 568/492
[58] Field of Search ............ 204/182.4, 131, 151, 204/182.3; 568/492

[56] References Cited

U.S. PATENT DOCUMENTS

| | | | |
|---|---|---|---|
| 3,165,415 | 1/1965 | Kilburn et al. | 204/182.4 |
| 3,270,062 | 8/1966 | Merz et al. | 260/601 |
| 3,507,764 | 4/1970 | Asahi et al. | 204/182.4 |
| 3,860,656 | 1/1975 | McCain, Jr. et al. | 260/601 R |
| 4,521,632 | 6/1985 | Wickenhaeuser et al. | 568/492 |
| 4,781,809 | 11/1988 | Falcone, Jr. | 204/182.4 |

FOREIGN PATENT DOCUMENTS 1130760 10/1968 United Kingdom .

OTHER PUBLICATIONS

Chemical Abstracts, vol. 94, No. 4, Jan. 26, 1981, p. 354, Zusammenfassung Nr. 20979v.

*Primary Examiner*—John F. Niebling
*Assistant Examiner*—Arun S. Phasge
*Attorney, Agent, or Firm*—John H. Shurtleff

[57] ABSTRACT

Aqueous glyoxal solutions which contain organic acids are purified by means of a membrane cell comprising two or more compartments by passing the glyoxal solution through at least one of the cell compartments separated from the neighboring compartment(s) by anion exchange membranes and by passing the aqueous solution of a base through at least one of the neighboring compartments.

12 Claims, No Drawings

PURIFICATION OF AQUEOUS GLYOXAL SOLUTIONS

The present invention relates to a process for purifying aqueous glyoxal solutions with the aid of a membrane cell.

Glyoxal, as is commonly known, is prepared by oxidizing acetaldehyde with nitric acid or by catalytic dehydrogenation of ethylene glycol. Either process produces an aqueous glyoxal solution which is contaminated with organic acids, such as formic acid, acetic acid, glycolic acid, glyoxylic acid and oxalic acid, and customarily has an acid number of from 5 to 200.

Since glyoxal, which is used as an auxiliary component in the textile and paper industry, must be very pure and have for example an acid number of < 1, there has been no shortage of proposals as to how the crude aqueous glyoxal solution might be purified.

According to U.S. Pat. No. 3,270,062, crude aqueous glyoxal solutions can be purified by treatment with solid ion exchangers. The disadvantage of this method resides in the costly regeneration of the ion exchanger, which must be carried out frequently because of the high acid values of the solutions.

U.S. Pat. No. 3,860,656 and DE-C-3,402,733 disclose that the acid impurities are removable by treating the crude aqueous glyoxal solutions with solutions of high molecular weight tertiary amines. The disadvantage here is the fact that the organic amine phase must be regenerated in a separate step, for example with aqueous solutions of alkaline agents.

U.S. Pat. No. 3,507,764 describes a membrane process wherein the concentration of organic acid in the crude glyoxal solution is reduced by electrodialysis. In this process, the aqueous crude glyoxal solution is passed through compartments of an electrodialysis cell which are bounded on one side by cation exchange membranes and on the other side by anion exchange membranes. This process is inadequate in that it permits the purification of only relatively dilute glyoxal solutions. For instance, if a more concentrated solution is used, for example a solution with a glyoxal content of about 40%, then about 25% of the glyoxal is lost through transfer into the concentrate compartments. The concentrating of the purified dilute glyoxal solution to obtain a commercial strength solution with a glyoxal content of 40% is associated with additional energy consumption.

It is an object of the present invention to provide a process whereby contaminated aqueous glyoxal solutions are converted, by avoiding the above-described disadvantages, into very highly concentrated purified glyoxal solutions having an acid number < 1.

We have found that this object is achieved by a process for purifying an aqueous glyoxal solution which contains an organic acid by means of a membrane cell comprising two or more compartments separated by ion exchange membranes, which comprises passing the glyoxal solution through at least one of the cell compartments separated from the neighboring compartment(s) by ion exchange membranes and passing the aqueous solution of a base through at least one of the neighboring compartments.

The novel process makes it possible to purify aqueous glyoxal solutions obtained for example by the conventional nitric acid oxidation of acetaldehyde or by dehydrogenation of glycol, which customarily have acid numbers of from 5 to 200. Suitable aqueous glyoxal solutions of the type mentioned have for example a glyoxal content of from 20 to 50, in particular from 35 to 45, % by weight.

The membrane cell used is a conventional installation containing up to 800, advantageously up to 500, compartments in a parallel arrangement separated by exchange membranes and gaskets. Preferably, the membrane cell contains from 1 to 400 compartments. The spacing between the membranes is from 10 to 0.4, preferably from 4 to 0.4, mm.

The base used is a water-soluble basic substance, advantageously an alkali metal salt, alkaline earth metal salt or ammonium salt of carbonic acid, such as the carbonate or bicarbonate of an alkali or alkaline earth metal or of ammonium or a quaternary ammonium carbonate or bicarbonate. The aqueous solution of the base used has a different pH, depending on the concentration. Preference is given to an aqueous base solution having a pH of 7.5 to 10, in particular from 8 to 8.5.

The process of the invention is carried out for example by passing the crude glyoxal solution to be purified through compartments $K_1$ and the aqueous solution of the base through compartments $K_2$ of a dialysis or electrodialysis cell comprising the sequence $$-(-K_2-M_1-K_1-M_1-)_n- \qquad \text{I}$$

where $M_1$ is an anion exchange membrane and n is from 1 to 800.

The dialysis cell with the above-identified sequence I can also be operated as an electrodialysis cell. In this case, the electric field is produced in a conventional manner by means of the two electrodes at either end of the membrane stack. The process of electrodialysis is carried out with direct current at a current density of from 0.1 to 10 $A/dm^2$, preferably from 0.5 to 3 $A/dm^2$. The direct voltage required for this purpose depends on the conductivities of the solutions and membranes and on the membrane spacing. The electrode rinse solution used is a conventional electrolyte for this purpose, such as a 0.5-10% strength aqueous sodium sulfate or sodium acetate solution.

The process of the invention can also be carried out in an electrodialysis cell comprising the characteristic sequence $$-(-M_2-K_2-M_1-K_1-M_1-K_3-)_n- \qquad \text{II}$$

by passing the aqueous glyoxal solution to be purified through compartments $K_1$, the aqueous base through compartments $K_2$ and basically any desired electrolyte through compartments $K_3$. $M_2$ is a bipolar membrane or a cation exchange membrane. $M_1$ and n are each as defined above.

In this case too the electric field is applied at the ends of the membrane stack as described above to carry out the electrodialysis as described above. But the electric field must be applied in such a way that the acid anions to be removed from $K_1$ are electrically transferred to $K_3$.

The electrolyte passing through compartments $K_3$ is an aqueous electrolyte, for example an aqueous solution of a salt such as sodium chloride or sodium sulfate or of an acid such as a lower carboxylic acid. Preference is given to using an aqueous solution of acetic acid or of an alkali metal salt of acetic acid, such as 0.5-0.1 N acetic acid or 0.5-0.1 N sodium acetate solution.

Suitable ion exchange membranes are conventional membranes, for example from 0.1 to 1 mm in thickness with a pore diameter of from 1 to 30 μm or a gellike structure. Anion exchange membranes are customarily constructed on the basis of a matrix polymer which contains chemically bonded cationic groups, while cation exchange membranes have a matrix polymer with anionic groups. Bipolar membranes have anionic groups on one surface and cationic groups on the other. Ion exchange membranes of the type mentioned are for example commercial polystyrene-based membranes available under the trade names SELEMION ® (Asahi Glass), NEOSEPTA ® (Tokoyama Soda) and IONAC ® (Ionac Chemical Company). The bipolar membrane can be fabricated for example by laying together cation and anion exchange membranes, by adhesively bonding together cation and anion exchange membranes (see for example DE-A-3,508,206) or as single film membranes, as described for example in U.S. Pat. No. 4,057,481.

The process according to the present invention, which may be carried out both continuously and batchwise, is operated at from 0° to 100° C., preferably at from 10° to 45° C., and at from 1 to 10 bar, preferably at atmospheric pressure. The solutions pass through the membrane cell at a flow velocity of from 0.001 to 2.0 m/s, preferably from 0.01 to 0.1 m/s.

The process according to the present invention, despite the high glyoxal concentration, surprisingly gives a high purification effect combined with a minimal glyoxal loss.

EXAMPLES 1 AND 2

A dialysis cell was used of type I, with n = 10, containing as membranes ($M_1$) commercial anion exchange membranes available under the trade name SELEMION ® AMV (from Asahi Glass). The dialysis cell was constructed in such a way that there was a compartment $K_2$ at either end. The effective area per membrane was 0.375 dm$^2$; the effective total membrane area of the dialysis cell thus was 7.5 dm$^2$. The space between neighboring membranes was 3 mm.

Recirculating via stock reservoir vessels at 25° C., the crude aqueous glyoxal solution to be purified was pumped through compartments K and 1000 g of a dilute aqueous solution of sodium bicarbonate at pH 8 was pumped through compartments $K_2$ until the pH of the glyoxal solution had risen to the desired value. Further particulars, such as the amounts used, the composition of the crude glyoxal solution, the experimental conditions and results are shown in the table.

EXAMPLES 3 TO 5

The equipment used was a dialysis cell as described in Examples 1 and 2 except that at either end of the membrane stack it was fitted with a platinum electrode, 35 cm$^2$ in surface area, and the associated electrode rinse circuits (the electrolyte used was a 5% strength aqueous sodium sulfate solution). The two electrolyte spaces were separated from the adjoining compartments $K_2$ by a cation exchange membrane commercially available under the trade name NAFION ® (Dupont). This electrodialysis cell was used to electrodialyze a crude glyoxal solution at 25° C. and a constant terminal voltage with decreasing current strength until the pH of the glyoxal solution had risen to the desired value. 1000 g of a dilute aqueous sodium bicarbonate solution (pH 8) were passed through compartments $K_2$ in the manner of Examples 1 and 2. The quantities used, the compositions of the crude glyoxal solutions, the experimental conditions and the results are shown in the table.

EXAMPLES 6 AND 7

The equipment used was an electrodialysis cell with the sequence $$—M_2—K_2—M_1—K_1—M_1—K_3—M_2—$$

the ends of which were the electrode rinse cycles of the catholyte and anolyte spaces. The membranes $M_1$ were anion exchange membranes commercially available under the trade name SELEMION ® AMV (from Asahi Glass), and membranes $M_2$ were bipolar membranes. The bipolar membranes had been obtained by laying together a SELEMION ® AMV anion exchange membrane and a SELEMION ® CMV cation exchange membrane. The effective membrane area was 3.14 cm$^2$. The space between the membranes was 1 cm.

The crude glyoxal solution was recirculated via a stock reservoir vessel through compartment $K_1$ at 34° C. 80 g of an aqueous sodium bicarbonate solution (c=0.5 eq/kg) were passed through compartment $K_2$. During the electrodialysis, the concentration of bicarbonate anions was maintained by the pH-controlled addition of carbon dioxide. A pH of from 8 to 8.2 was maintained at the same time. In a third cycle, 80 g of dilute acetic acid (c=0.1 eq/kg) were pumped through compartment $K_3$. The electrodes were rinsed with 150 g of recirculating dilute aqueous sodium acetate solution (c=0.1 eq/kg).

The electrodialysis was carried out a constant terminal voltage and decreasing current strength (cf. table) until the pH of the glyoxal solution had risen to the desired value. Quantities used and composition of the crude glyoxal solutions, experimental conditions and results are shown in the table.

EXAMPLE 8

The equipment used was the electrodialysis cell described in Examples 6 and 7 except that the bipolar membranes $M_2$ had been replaced by cation exchange membranes commercially available under the trade name SELEMION ® CMV (from Asahi Glass).

Recirculating via stock reservoir vessels, the crude glyoxal solution was pumped at 30° C. through compartment $K_1$, 80 g of a dilute aqueous sodium bicarbonate solution (pH 8) were pumped through compartment $K_2$, and 80 g of a dilute aqueous sodium acetate solution (c =0.1 eq/kg) were pumped through compartment $K_3$. The electrode rinse cycle comprised 150 g of recirculating dilute aqueous sodium sulfate solution (c =0.1 eq/kg). The membranes used had an effective area of 3.14 m$^2$, and the membrane spacing was 1 cm. The electrodialysis was carried out at constant terminal voltage and decreasing current strength (cf. table) until the pH of the glyoxal solution had risen to the desired value. The quantity and composition of the crude glyoxal solution, experimental conditions and results are shown in the table.

RESULTS OF EXAMPLES 1-8

| | Amount (g) | Glyoxal concentration (% by weight) | pH | AN[1] | $\chi^2$ (ms/cm) | Terminal voltage (V) | Current (mA) | Time (h) | Charge quantity (Ah) | Yield of material (%) | Acid depletion (%) |
|---|---|---|---|---|---|---|---|---|---|---|---|
| Crude glyoxal Inflow Examples 1-4 | 1000 | 40 | 1.3 | 13 | | | | | | | |
| Outflow Example 1 | 1039 | 34.8 | 5.5 | 0.17 | 0.22 | — | — | 13.5 | — | 90 | 99 |
| Outflow Example 2 | 1060 | 37.5 | 3 | 1.7 | 0.20 | — | — | 10.0 | — | 99 | 87 |
| Outflow Example 3 | 1038 | 37.4 | 3 | 1.1 | 0.15 | 50 | 330-230 | 6.5 | 1.6 | 96 | 91 |
| Outflow Example 4 | 1043 | 37.4 | 5.7 | 0.34 | 0.19 | 100 | 640-470 | 5.7 | 3.1 | 97 | 97 |
| Crude glyoxal Inflow Example 5 | 1000 | 42 | 1.5 | 6.6 | | | | | | | |
| Outflow Example 5 | 1026 | 40 | 5.0 | 0.61 | 0.15 | 50 | 290-190 | 5.5 | 1.1 | 97 | 91 |
| Crude glyoxal Inflow Example 6 | 60 | 40.5 | 1.45 | 9.3 | 0.68 | | | | | | |
| Outflow Example 6 | 60 | 39.5 | 5 | 0.59 | 0.23 | 150 | 110-50 | 8 | 0.62 | 97 | 94 |
| Crude glyoxal Inflow Example 7-8 | 60.5 | 42.2 | 1.55 | 6.25 | 0.78 | | | | | | |
| Outflow Example 7 | 60.8 | 40.7 | 5.1 | 0.67 | 0.15 | 150 | 143-49 | 5.5 | 0.41 | 97 | 89 |
| Outflow Example 8 | 60.7 | 41.2 | 5.1 | 0.74 | 0.14 | 100 | 138-54 | 4.8 | 0.39 | 98 | 88 |

[1] AN: acid number mg of KOH/g of substance
[2] conductivity

We claim:

1. In a process for purifying a crude aqueous glyoxal solution to remove organic acid impurities by passing the crude solution through a dialysis or electrodialysis cell containing a plurality of compartments separated from each other by ion exchange membranes, the improvement which comprises:

passing said crude glyoxal solution through a compartment $K_1$ and passing an aqueous solution of a base through a compartment $K_2$ of said dialysis or electrodialysis cell which is arranged according to the sequence $$-(-K_2-M_1-K_1-M_1-)_n-$$

where $M_1$ is an anion exchange membrane and n is an integer of from 1 to 800.

2. A process as claimed in claim 1, wherein the aqueous solution of a base is the aqueous solution of an alkali metal, alkaline earth metal or an ammonium carbonate or bicarbonate.

3. A process as claimed in claim 1, wherein the solutions passed through the compartments of the membrane cell flow past the membrane surface at a flow velocity of from 0.001 to 2 meters per second.

4. A process as claimed in claim 1, wherein the glyoxal solution to be purified has a glyoxal content of from 20 to 50% by weight and an acid number of from 5 to 200.

5. A process as claimed in claim 1, wherein the aqueous base solution has a pH of 7.5 to 10.

6. A process as claimed in claim 1, wherein the aqueous base solution has a pH of 8 to 8.5.

7. In a process for purifying a crude aqueous glyoxal solution to remove organic acid impurities by passing the crude solution through an electrodialysis cell containing a plurality of compartments separated from each other by ion exchange membranes, the improvement which comprises:

passing said crude glyoxal solution through a compartment $K_1$ while passing an aqueous solution of a base through a compartment $K_2$ and an aqueous electrolyte through a compartment $K_3$ of said electrodialysis cell which is arranged according to the sequence $$-(-M_2-K_2-M_1-K_1-M_1-K_3-)_n-$$

where $M_1$ is an anion exchange membrane, $M_2$ is a bipolar membrane or a cation exchange membrane and n is an integer of from 1 to 800.

8. A process as claimed in claim 7, wherein the aqueous base solution has a pH of 7.5 to 10.

9. A process as claimed in claim 7, wherein the aqueous base solution has a pH of 8 to 8.5.

10. A process as claimed in claim 7, wherein the aqueous solution of a base is the aqueous solution of an alkali metal, alkaline earth metal or an ammonium carbonate or bicarbonate.

11. A process as claimed in claim 7, wherein the solutions passed through the compartments of the membrane cell flow past the membrane surface at a flow velocity of from 0.001 to 2 meters per second.

12. A process as claimed in claim 7, wherein the glycol solution to be purified has a glyoxal content of from 20 to 50% by weight and an acid number of from 5 to 200.

* * * * *